United States Patent [19]

Huggins et al.

[11] Patent Number: 4,469,684

[45] Date of Patent: Sep. 4, 1984

[54] STORAGE STABLE TOPICAL PHARMACEUTICAL COMPOSITION CONTAINING ZINC ERYTHROMYCIN AND LOW DIELECTRIC SOLVENTS

[75] Inventors: James E. Huggins, Madeira; Mary L. Batt, Wyoming; William J. Kozarek, Cincinnati, all of Ohio

[73] Assignee: The Procter & Gamble Company, Cincinnati, Ohio

[21] Appl. No.: 434,649

[22] Filed: Oct. 15, 1982

[51] Int. Cl.³ .............................................. A61K 31/71
[52] U.S. Cl. .................................... 424/181; 424/145; 424/289
[58] Field of Search .................... 424/181, 145, 289

[56] References Cited

U.S. PATENT DOCUMENTS

| | | | |
|---|---|---|---|
| 3,472,931 | 10/1969 | Stoughton | 424/180 |
| 3,562,806 | 2/1971 | Grant et al. | 424/35 |
| 3,927,197 | 12/1975 | Monkhouse | 424/45 |
| 4,000,263 | 12/1976 | Hebborn | 424/181 |
| 4,006,218 | 2/1977 | Sipos | 424/54 |
| 4,261,982 | 4/1981 | Luedders et al. | 424/181 |

FOREIGN PATENT DOCUMENTS 889,327 10/1981 Belgium .
2383667 10/1978 France .

OTHER PUBLICATIONS

Goldberg—Antibiotics, Their Chemistry and Non—Medical Uses, p. 102, 1959.
Balsam et al.—Cosmetics, Science & Technology, 2nd ed., vol. 1, pp. 42–43, 1972.
Chemical Abstracts 55:13767.

Primary Examiner—Leonard Schenkman
Attorney, Agent, or Firm—Steven J. Goldstein; Jack D. Schaeffer; Richard C. Witte

[57] ABSTRACT

A storage stable topical pharmaceutical composition containing zinc erythromycin, particularly useful in the topical treatment of acne vulgaris, is disclosed. This composition contains a solvent having a dielectric constant, measured at 25° C., of from about 5.5 to about 15, preferably from about 8 to about 12, such as t-butanol, to impart storage stability to the zinc erythromycin component. The composition may additionally contain particularly selected pharmaceutically-acceptable nitrogen-containing stabilizer components, such as diisopropanolamine.

12 Claims, No Drawings

STORAGE STABLE TOPICAL PHARMACEUTICAL COMPOSITION CONTAINING ZINC ERYTHROMYCIN AND LOW DIELECTRIC SOLVENTS

TECHNICAL FIELD

The present invention relates to topical pharmaceutical compositions which are useful in the treatment of skin dermatoses, particularly in the treatment of acne vulgaris. These compositions contain zinc erythromycin as the active pharmaceutical component and exhibit excellent storage stability.

BACKGROUND OF THE INVENTION

Acne vulgaris and other types of acne and acneiform skin maladies associated with hyperplasia of the sebaceous follicle are often treated by the oral administration of antibiotics. While oral administration of these drugs often constitutes an effective treatment regimen for acne, oral therapy has several disadvantages. For example, oral administration subjects the entire body to the antibiotic composition while only the localized acne lesion actually requires treatment. Moreover, almost all antibiotics have some undesirable side effects when taken orally. In contrast with oral dosing in the treatment of acne, topical application of antibiotics delivers the antibiotic to the afflicted situs and minimizes the antibiotic levels in the circulatory and gastrointestinal systems. Properly administered, the therapeutic benefit of topical antibiotic therapy in treating skin disorders can be comparable with, or superior to, that achieved by oral antibiotic therapy, while avoiding the undesirable side effects of oral administration.

The antibiotic erythromycin has frequently been proposed for topical use in the treatment of acne. However, erythromycin is known to have relatively poor storage stability when formulated in topical vehicles, making the formulation of such topical products difficult. Even more preferred for the topical treatment of acne, in terms of increased efficacy, is zinc erythromycin. However, the formulation of topical products containing zinc erythromycin presents an even greater storage stability problem since the presence of zinc in the composition acts to catalyze the erythromycin decomposition reaction. In the past, it has been proposed that this stability problem be handled by marketing zinc erythromycin products as separate pharmaceutical active and topical vehicle components which are mixed together into a single composition by the pharmacist immediately prior to dispensing to the patient. Such a technique for maximizing the shelf stability of topical zinc erythromycin compositions is, at best, cumbersome, and leads to the possibility of variations in the level of active component, as the composition is formulated by the pharmacist. It, therefore, would be highly desirable to be able to formulate a single phase dosage form in which the zinc erythromycin component exhibits extended shelf life stability.

U.S. Pat. No. 4,261,982, Luedders and Willins, issued Apr. 14, 1981, describes pharmaceutical compositions, especially useful in the topical treatment of acne, containing mixtures of zinc salts with erythromycin (zinc erythromycin). It is taught that these compositions may contain any of the common, non-water-based cosmetic topical carriers; a wide variety of such carriers is generically disclosed.

U.S. Pat. No. 3,562,806, Grant, et al, issued Feb. 9, 1971, describes a method and compositions for administration of pharmaceuticals to ruminants so as to avoid decomposition and deactivation of the pharmaceuticals. The pharmaceuticals are coated with the reaction product of an organic nitrogen-containing base, such as ethanolamine or diethanolamine, and an unsaturated cellulose derivative; the preferred coating material is cellulose propionate 3-morpholinobutyrate.

Belgian Pat. No. 889,327, Rorer International (Overseas) Inc., published Oct. 16, 1981, describes compositions for the topical treatment of acne containing an organic acyl peroxide together with an erythromycin compound. Some of the exemplified compositions include low levels of diisopropanolamine. These formulations are packed as separate carrier and erythromycin active components, with the two components being mixed together just prior to use.

U.S. Pat. No. 3,472,931, Stoughton, issued Oct. 14, 1969, describes compositions for enhancing the skin penetration of pharmaceutical actives, such as erythromycin, using lower alkyl amides, such as N,N-dimethyl acetamide or N,N-diethyl acetamide.

U.S. Pat. No. 4,000,263, Hebborn, issued Dec. 28, 1976, recognizes that erythromycin base exhibits poor stability in solution and provides topical compositions yielding improved stability of the erythromycin over prolonged periods of time. These compositions comprise erythromycin base, propylene glycol, ethanol, and an ethoxylated ether of lauryl alcohol.

U.S. Pat. No. 3,927,197, Monkhouse, issued Dec. 16, 1975, describes pharmaceutical compositions containing E-series prostaglandins together with saturated tertiary aliphatic alcohols having 4 to 10 carbon atoms, such as t-butanol, as a stabilizing component.

U.S. Pat. No. 4,006,218, Sipos, issued Feb. 1, 1977, describes antimicrobial compositions, having enhanced activity, containing an antimicrobial agent, such as erythromycin, together with a potentiator, such as a primary, secondary or tertiary monohydric alcohol having a straight chain of from 5 to 10 carbon atoms.

French Pat. No. 2,383,667, Desjonqueres, published Oct. 13, 1978, describes compositions for the topical treatment of acne comprising erythromycin base or salts together with a hydrating excipient, such as chloroform.

Chemical Abstracts 55:13767 describes a study indicating that barbiturates in aqueous solution may be stabilized by lowering the dielectric constant of the solution. In the experiments, the dielectric constant of various solutions tested was lowered by the addition of methanol, ethanol, polyalcohols or sugars.

By the present invention, novel zinc erythromycin compositions characterized by enhanced storage stability properties are provided. The compositions can be formulated as a single package product without any significant risk of decomposition of the zinc erythromycin active over the typical product shelf life (for example, one to three years). The compositions herein are suitable for human and veterinary uses. They exhibit antifungal activity and are especially useful when applied topically in the treatment of acne.

SUMMARY OF THE INVENTION

The present invention encompasses stable topical pharmaceutical compositions, preferably having a pH between about 7 and about 10, comprising:

(a) a safe and effective amount of zinc erythromycin; and
(b) from about 50% to about 99% of a pharmaceutically-acceptable solvent having a dielectric constant measured at 25° C., of from about 5.5 to about 15, preferably of from about 8 to about 12, the most preferred solvent being t-butanol.

These compositions may additionally, preferably, include the nitrogen-containing stabilizer components selected from amine or ammonium compounds having pendant from the nitrogen atom no more than two long chains (i.e., greater than $C_{12}$), preferably no more than one long chain; preferred stabilizers include diisopropanolamine, mono-ethanolamine, 2-amino-2-methyl-1-propanol, diethylamine, N,N-dimethylethanolamine, triethylamine, triethanolamine, cetyl pyridinium chloride, di-$C_{10}$ dimethylammonium chloride, $C_{20}$ ammonium hexanoate, 1-dimethylamino-2-propanol, 3-dimethylamino-1-propanol, lecithin, and mixtures thereof.

DETAILED DESCRIPTION OF THE INVENTION

As used herein, the following terms have the definitions given below.

By "topical application" is meant directly spreading, spraying or laying of a compound or composition onto epidermal tissue. Topical application can be achieved by rubbing, applicator pads, containers with applicator fitments, sprays or any other convenient means.

By "safe and effective amount" is meant an amount of a compound or composition which is effective to alleviate the inflammation and lesions of acne or acneiform skin diseases and yet causes no undersirable side effects (at a reasonable benefit/risk ratio). For topical application, a dose range of a topical composition formulated in the manner of this invention of from about 0.01 to about 25 milligrams/square centimeter/day is effective. The dosage will vary with the patient, depending upon such factors as the type and severity of the skin disorder, the age, health and physical condition of the patient, the content of zinc erythromycin in the composition, the use of vehicles which enhance skin penetration of the active, the frequency of application, the area of the body which is afflicted, and like factors within the knowledge of the attending physician. Generally, the compositions applied will provide from about 0.0001 to about 12.5 milligrams/square centimeter of the zinc erythromycin compound; these compositions would generally be applied to the afflicted situs once or twice daily to afford relief from acneiform skin afflictions. Similar quantities are useful in the topical treatment of other skin disorders and dermatoses of bacterial origin, e.g., impetigo (impetigo contagiosa) or ecthyma; bullous impetigo; scalded skin syndrome (dermatitis exfoliative); erysipelas; folliculitis (including furuncles/carbuncles); hidradenitis suppurativa; paronychial infections; erythrasma; and the like.

By "comprising" herein is meant that various other compatible ingredients can be present in the present compositions in such proportions as will not adversely affect the stability and penetrating effectiveness of the zinc erythromycin compositions. The term "comprising" thus encompasses and includes the more restrictive terms "consisting" and "consisting essentially of" within its scope.

By "pharmaceutically-acceptable" is meant that stabilizer components, solvents and the other ingredients used in the compositions are suitable for use in contact with the tissues of humans and lower animals without undue toxicity, irritation, allergic response, and the like, commensurate with a reasonable benefit/risk ratio.

By "compatible" is meant that the components of the present invention are capable of being commingled without interacting in a manner which would substantially decrease either the pharmaceutical efficacy of the zinc erythromycin component or the stability of the composition under ordinary storage and usage conditions.

All percentages and ratios used herein are by weight, unless otherwise specified.

The zinc erythromycin component utilized in the compositions of the present invention is the product of the mixture of an erythromycin compound, especially erythromycin base, with zinc or zinc compounds, preferably zinc salts, especially the zinc salts of carboxylic acids, e.g., zinc acetate, zinc propionate, zinc valerate, zinc 2-ethyl hexanoate and the like. While not intending to be limited by theory, both polarography and NMR spectrography suggest that this mixture may lead to complex formation between the erythromycin and the zinc salt. Infrared analysis shows small shifts consistent with complex formation, and X-ray crystallography shows a distinct pattern for a mixture of zinc acetate with erythromycin base which differs from patterns for either zinc acetate or erythromycin base.

Zinc erythromycin is known in the art and is taught to be effective in the topical treatment of acneiform skin dermatoses. The description of the compound, the manner in which it is used and the method of making it are set forth in detail in U.S. Pat. No. 4,261,982, Luedders and Willins, issued Apr. 14, 1981, incorporated herein by reference.

The erythromycin compounds used in forming zinc erythromycin include "erythromycin base", which is the antibiotic produced by the strain streptomyces erythreus, erythromycin base in the form of hydrated crystals, as well as other compounds of erythromycin, i.e., the well-known salts of erythromycin base with acids and the ester derivatives of erythromycin. Non-limiting examples of commercially-available compounds of erythromycin include: erythromycin estolate, which the lauryl sulfate salt of the propionic acid ester of erythromycin; erythromycin glucoheptonate, which is the glucoheptonic acid salt of erythromycin; erythromycin lactobionate, which is prepared from erythromycin base and lactobiono-delta-lactone; erythromycin propionate, the propionic acid ester of erythromycin; erythromycin stearate, which includes both the stearic acid salt of erythromycin and the stearic acid ester of erythromycin; and erythromycin ethyl succinate, which is the ester of erythromycin and ethyl succinic acid.

The zinc compounds employed in producing zinc erythromycin can be selected from any of the toxicologically-acceptable zinc salts; the zinc salts of carboxylic acids are preferred. Non-limiting examples of typical zinc salts which can be used in the practice of this invention include the zinc salts of $C_1$-$C_{12}$ carboxylic acids and polycarboxylic acids, including zinc acetate, zinc propionate, zinc butyrate, zinc pentanoate, zinc hexanoate, zinc heptanoate, zinc 2-ethyl hexanoate, zinc octanoate, zinc nonanoate, zinc decanoate, zinc undecanoate, and zinc dodecanoate. Other zinc salts useful herein include the zinc salts of amino acids, such as zinc alanine, zinc methionine, zinc glycine, zinc asparagine, zinc aspartine, zinc serine, and the like. Other zinc salts useful herein include zinc citrate, zinc maleate, zinc benzoate, zinc acetylacetonate, zinc chloride, zinc sulfate, zinc phosphate, zinc bromide, and the like. The zinc chalcogens can also be used herein, but are not preferred since they do not interact rapidly with erythromycin. Likewise, the more acidic zinc salts, such as zinc chloride, are not preferred for use herein since they do not appear to penetrate the skin optimally. Highly preferred for use herein are zinc salts of the shorter chain ($C_2$–$C_8$) carboxylic acids and zinc acetylacetonate. Especially preferred for use herein are zinc acetate, zinc acetylacetonate, and zinc 2-ethyl hexanoate (known commercially as "zinc octoate").

Preparation of the zinc erythromycin component is achieved by simply admixing a zinc compound of the foregoing type with erythromycin base or other erythromycin compound in a convenient reaction medium. By convenient reaction medium is meant any solid or liquid system in which the zinc or zinc compound and erythromycin or erythromycin compound can be admixed in reactive form. For example, ethanol is a convenient reaction medium for zinc acetate and erythromycin base, even though zinc acetate is only sparingly soluble in ethanol, because the addition of erythromycin immediately draws the zinc acetate into solution as the zinc erythromycin acetate complex. Thus, non-aqueous polar solvents, e.g., alcohols, such as ethanol, constitute appropriate reaction media. The zinc erythromycin component is formed at room temperature, under extremely mild conditions, based on about a 1:1 mole ratio of zinc salt and erythromycin compound.

Because it has been determined that the storage stability of zinc erythromycin is adversely affected by the presence of ethanol, unless the compositions are refrigerated, the compositions herein are preferably ethanol-free, i.e., contain less than about 1% ethanol. However, it should be noted that the nitrogen-containing stabilizers, described herein, can enhance the stability of zinc erythromycin in ethanol, thus permitting the inclusion of higher ethanol levels. It has also been determined that the storage stability of the present compositions is adversely affected by the presence of water. Accordingly, the compositions herein are preferably water-free, i.e., contain less than about 1% water. Finally, in order to optimize the stability of the erythromycin component, it is preferred that the present compositions have a pH of from about 7 to about 10.

The zinc erythromycin component is included in the compositions of the present invention in a safe and effective amount; preferably, the compositions of the present invention contain from about 0.3% to about 15%, more preferably from about 2% to about 10% of the zinc erythromycin component (i.e., the mixture of zinc compound and erythromycin compound).

The compositions of the present invention also contain from about 50% to about 99%, preferably from about 65% to about 95%, of a pharmaceutically-acceptable compatible topical carrier. Compatible carriers used with the zinc erythromycin active ingredients in the topical compositions of this invention can comprise any cosmetic carrier which does not impair the efficacy of the zinc erythromycin component or the nitrogen-containing stabilizer component, and which is not irritating or otherwise detrimental to the afflicted situs. In general, any of the common, non-water based cosmetic carriers may be used herein. Typical carriers include short chain alcohols and ketones and emollients, such as hydrocarbon oils and waxes, lanolin and lanolin derivatives, silicone oils, monoglyceride, diglyceride and triglyceride esters, fatty acids, fatty alcohols, alkyl and alkenyl esters of fatty acids, alkyl and alkenyl diesters of dicarboxylic acids, polyhydric alcohols and their ether and ester derivatives, wax esters, and beeswax derivatives. Preferred carriers contain materials which enhance the delivery of erythromycin through the skin. These include the alkyl and alkenyl esters of fatty acids, such as isopropyl myristate; alkyl and alkenyl diesters of dicarboxylic acids, such as diisopropyl sebacate; fatty alcohols, such as lauryl alcohol; and ester derivatives of polyhydric alcohols, such as propylene glycol dipelargonate. A particularly preferred carrier material is diisopropyl sebacate (DIPS). Combinations of diisopropyl sebacate with pharmaceutically-acceptable lower alcohols, are described in U.S. Pat. No. 4,299,826, Luedders, issued Nov. 1981, incorporated herein by reference.

All or part of the topical carrier component used in the present invention consists of a solvent material having a dielectric constant of from about 5.5 to about 15, preferably from about 8 to about 12, when measured at 25° C. This solvent may consist of a mixture of solvents, some or all of which have dielectric constants falling outside the defined range, as long as the dielectric constant of the mixture falls within that range (for example a combination of polysiloxane, having a dielectric constant of about 2 (e.g., Silicone D4), with i-propanol in an appropriate ratio can constitute a preferred solvent for use herein). It has been found that when such low dielectric constant solvents are used, the storage stability of the zinc erythromycin component in the compositions is dramatically increased. Higher dielectric constant solvents yield decreased stability of the zinc erythromycin component. Solvents having dielectric constants lower than the range specified generally exhibit a low solubility for the zinc erythromycin active thereby delivering dosages of the active which are too low for effective treatment. These benefits are optimized when the dielectric constant is in the range of from about 8 to about 12. Clearly, the solvent should be chosen such that the zinc erythromycin component is soluble in it. Further, in order to obtain optimum stability, it is preferred that the low dielectric constant solvent selected have a pH and be used in such an amount that the entire composition has a pH of from about 7 to about 10. Finally, it is preferred that the low dielectric constant solvent be non-cyclic in structure; benzyl alcohol, which has an appropriate dielectric constant for use in this invention, is not as effective in stabilizing zinc erythromycin as, for example, t-butanol.

Dielectric constant is the property of a solvent which quantifies the amount of energy required to separate two oppositely charged bodies in the solvent as compared to the energy required to separate the same two oppositely charged bodies in a vacuum. By definition, the dielectric constant of a vacuum is unity. The dielectric constant of water at 25° C. is 78.5, thus it takes 78.5 times more energy to separate two oppositely charged bodies in a vacuum than in water. This property is closely related to the polarity of the solvent. The dielectric constants of most pharmacuetical solvents are known, values for a number of binary and tertiary blends have been reported, and, if not reported, can be readily estimated. See, The Handbook of Chemistry and Physics. 45th ed. The Chemical Rubber Company, Cleveland, Ohio, 1964, pp. 30–33; Margott, A.A. and Smith, E.R. Table of Dielectric Constants of Pure Liquids, N.B.S. Circ. 514, U.S. Government Printing Office, Washington, D.C. 1951; and Moore, W.E., J.A. Ph. A. (Sci), 47:855 (1958), all of which are incorporated herein by reference. The following table gives the dielectric constants, measured at 25° C., for a selected group of solvents.

TABLE 1

Dielectric Constants (at 25° C.) of Various Solvents

| Solvent | Value |
|---|---|
| Methanol | 33.5 |
| Ethanol | 24.3 |
| n-Propanol | 20.1 |
| i-Propanol | 18.0 |
| t-Butanol | 9.9 |
| Ethylene Glycol | 37.7 |
| Glycerin | 40.1 |
| Acetone | 19.1 |
| Dioxane | 2.1 |
| i-Amyl Alcohol | 14.7 |
| Amyl Alcohol | 13.9 |
| t-Amyl Alcohol | 5.8 |
| Chloroform | 4.8 |

The compositions of the present invention contain from about 50% to about 99%, more preferably from about 55% to about 80%, of the low dielectric constant solvents. Preferred low dielectric constant solvents for use herein include t-butanol, i-amyl alcohol, t-amyl alcohol and amyl alcohol, with the most preferred being t-butanol. Particularly preferred are compositions containing t-butanol together with diisopropyl sebacate (DIPS) as a cosolvent, with the cosolvent being present in the composition in an amount of from about 1% to about 45%, preferably from about 15% to about 35%, of the total composition.

The compositions of the present invention may also contain from about 0.1% to about 10%, preferably from about 0.5% to about 5%, more preferably from about 1% to about 3%, of a pharmaceutically-acceptable nitrogen-containing stablizer component. These stabilizers are described in concurrently-filed U.S. patent application Ser. No. 434,650, Storage Stable Topical Pharmaceutical Compositions Including Nitrogen-Containing Stabilizers, Batt, Huggins and Kozarek, incorporated herein by reference. This component acts to provide storage stability over an extended period of time for the zinc erythromycin pharmaceutical active; it should, therefore, be chosen so that the zinc erythromycin component is soluble in it or in its admixture with the topical carrier. The stabilizer component must contain a nitrogen atom which is sterically available to complex with the zinc compound in solution, thereby preventing the interaction between zinc and erythromycin which leads to the erythromycin decomposition reaction. Since it appears that the stabilizer molecules complex both above and below the molecular plane of the zinc compound, it is believed that the optimum molar ratio of stabilizer to zinc compound in the compositions of the present invention is about 2:1. In order to minimize steric hindrance around the nitrogen, the stabilizers useful herein comprise amine or ammonium compounds having pendant from the nitrogen atom no more than two long chains and preferably no more than one long chain (i.e., substituted or unsubstituted, saturated or unsaturated chains containing more than twelve carbon atoms), or mixtures of such compounds. Amines may contain three short chains (i.e., $\leq C_{12}$), two short and one long chain or, less preferably, one short and two long chains. Ammonium compounds may contain four short chains, three short chains and one long chain or, less preferably, two short chains and two long chains. Preferred examples of such compounds include mono-$C_1$-$C_6$ saturated or unsaturated alkyl, hydroxyalkyl or alkylamido amines, di-$C_1$-$C_6$ saturated or unsaturated alkyl, hydroxyalkyl or alkylamido amines, tri-$C_1$-$C_6$ saturated or unsaturated alkyl, hydroxyalkyl or alkylamido amines, mono-$C_1$-$C_{16}$ saturated or unsaturated alkyl, hydroxyalkyl or alkylamido pyridinium compounds, mono-$C_1$-$C_{16}$ saturated or unsaturated alkyl, hydroxyalkyl or alkylamido amine oxides, and mono-$C_1$-$C_{20}$ saturated or unsaturated alkyl, hydroxyalkyl or alkylamido ammonium compounds. The most preferred stabilizer components are selected from the group consisting of diisopropanolamine, monoethanolamine, 2-amino-2-methyl-1-propanol, diethylamine, N,N-dimethylethanolamine, triethylamine, triethanolamine, cetyl pyridinium chloride, di-$C_{10}$ dimethylammonium chloride, $C_{20}$ ammonium hexanoate, 1-dimethylamino-2-propanol, 3-dimethylamino-1-propanol, lecithin (phosphatidyl choline), and mixtures thereof. The most preferred stabilizer component for use in the present invention is diisopropanolamine.

Optional components at art-established levels of from about 0.001% to about 25% of the topical compositions can be used to provide benefits thereto. Such optional components are well-known in the art and include, but are not limited to, common thickening agents, such as crosslinked polymethylene polymers, cellulosic polymers, clays, various gums, microcrystalline waxes, polyethylene glycols; fragrance materials; coloring agents; preservatives; anti-oxidants and the like.

Topical treatment regimens according to the practice of this invention comprise applying the compositions herein directly to the skin at the situs of the dermatosis. The rate of application and duration of treatment will depend upon the severity of the condition, the response of the particular patient, and related factors within the sound medical judgment of the attending physician or patient. In general, for the compositions within the component ranges noted above, application rates of from about 0.01 to about 25 milligrams/square centimeter of afflicted situs per day are used. Application can be made once, or preferably several times, daily for periods of a week or more, to relieve dermatoses and to promote wound healing .

The following examples illustrate preferred topical compositions prepared and used in the manner of this invention, but are not intended to be limiting thereof.

EXAMPLE I

Using the method described below and the formulations set forth in the table, the storage stability of a variety of zinc erythromycin topical formulations of the present invention were compared to similar compositions formulated as described in the art.

1. Formulation (a) Concentrations listed in the table below are approximate. The solid form components were weighed out on a top-loading balance and added to the liquid components (e.g., the vehicle) without correcting for their solution volume. The liquids were dispensed by both volume and weight. Each of the compositions numbered 8 through 37 had pH's between about 7 and about 10.

(b) Dissolution was made at room temperature using vigorous mixing.

2. Sample Storage (a) Samples were stored at 60° C. and/or 80° C. in a constant temperature oven.

(b) All samples were stored in glass bottles. Some of the compositions were stored in a single container (in which case an aliquot of the composition was taken at each analysis time) or in multiple containers (in which case one container was used for each set of analyses).

(c) The samples were analyzed on a daily to weekly schedule depending upon the expected rate of degradation of the composition.

3. Sample Analysis (a) The samples were allowed to equilibrate at room temperature prior to analysis.

(b) The samples were then analyzed by HPLC for erythromycin.

4. Calculation (a) Erythromycin degradation was assumed to follow first order kinetics where $$\ln C/C_o = kt$$

$C$ = concentration at time t,
$C_o$ = initial concentration,
$k$ = degradation rate constant, and
$t$ = time in days.

(b) The degradation rate constant for each composition was calculated by curve fitting multiple data points (3 to 5 points per composition) to the above degradation equation.

(c) The number of days required for degradation of 10% of erythromycin component, at room temperature, was then estimated for each composition using the computed rate constant. This was done by extrapolating a degradation curve for the composition at room temperature based on the degradation rates for that composition at 60° C. and 80° C. Rate constants can be used to accurately compare the relative stabilities of two formulations. However, the stability time predictions are only estimates based on these rate constants.

The compositions tested and the storage stability performance of each of these compositions is set forth in the following table.

| COMPOSITION | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Erythromycin Base (mg/ml) | 48 | 48 | 40 | 48 | 40 | 48 | 40 | 48 | 40 | 48 | 44 | 40 | 48 | 44 | 40 | 40 | 40 |
| Zinc Acetate (mg/ml) | — | — | — | — | 12 | — | — | — | — | — | — | — | 12 | 12 | 12 | — | 12 |
| Zinc Octoate (mg/ml) | 19 | 19 | 19 | 12 | — | 19 | 19 | 19 | 19 | 19 | 19 | 19 | — | — | — | 19 | — |
| DIPS (μl/ml) | 270 | 270 | 270 | 270 | 270 | 270 | 270 | 270 | 270 | 270 | 270 | 270 | 270 | 270 | 270 | 270 | 270 |
| Methanol (μl/ml) | 690 | — | — | — | — | — | — | — | — | — | — | — | — | — | — | — | — |
| Ethanol (μl/ml) | — | 690 | — | 690 | 690 | — | — | — | — | — | — | — | — | — | — | — | — |
| Isopropanol (μl/ml) | — | — | — | — | — | 690 | 690 | — | — | — | — | — | 690 | 690 | 690 | — | — |
| t-butanol (μl/ml) | — | — | — | — | — | — | — | 515 | 515 | 690 | 690 | 690 | — | — | — | 515 | 515 |
| Silicone D4 (μl/ml) | — | — | — | — | — | — | — | 175 | 175 | — | — | — | — | — | — | 175 | 175 |
| Rate Constant 60° C. | −.6579 | −.0578 | −.1083 | — | — | −.0113 | −.0087 | −.0085 | −.0037 | −.0460 | −.0468 | −.0028 | −.1122 | — | −.0080 | −.0027 | −.0143 |
| Predicted days to 90% at RT | * | 85 | 46 | — | — | 330 | 630 | 650 | 1500 | 830 | 825 | 2000 | 325 | — | 690 | 2100 | 375 |
| Rate Constant 80° C. | — | — | −.3544 | −1.8326 | −2.3567 | −.0972 | −.0909 | −.0841 | −.0693 | — | — | −.0309 | — | −.1296 | −.1013 | −.0332 | −.1036 |
| Predicted days to 90% at RT | — | — | 95 | * | * | 375 | 420 | 440 | 550 | — | — | 1300 | — | 290 | 360 | 1200 | 350 |

| COMPOSITION | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|
| Erythromycin Base (mg/ml) | 44 | 44 | 44 | 44 | 44 | 44 | 44 | 44 | 44 | 44 | 44 | 44 | 44 | 44 | 44 | 44 | 44 | 44 | 44 | 44 |
| Zinc Acetate (mg/ml) | 12 | 12 | 12 | 12 | 12 | 12 | 12 | 12 | 12 | 12 | 12 | 12 | 12 | 12 | 12 | 12 | 12 | 12 | 12 | 12 |
| Zinc Octoate (mg/ml) | — | — | — | — | — | — | — | — | — | — | — | — | — | — | — | — | — | — | — | — |
| DIPS (μl/ml) | 270 | 270 | 270 | 270 | 270 | 270 | 270 | 270 | 270 | 270 | 270 | 270 | 270 | 270 | 270 | 270 | 270 | 270 | 270 | 270 |
| Methanol (μl/ml) | — | — | — | — | — | — | — | — | — | — | — | — | — | — | — | — | — | — | — | — |
| Ethanol (μl/ml) | — | — | — | — | — | — | — | — | — | — | — | — | — | — | — | — | — | — | — | — |
| Isopropanol (μl/ml) | — | — | — | — | — | — | — | — | — | — | — | — | — | — | — | — | — | — | — | — |
| t-butanol (μl/ml) | 685 | 680 | 690 | 690 | 680 | 685 | 685 | 685 | 685 | 685 | 685 | 685 | 680 | 670 | 685 | 685 | 680 | 670 | 685 | 685 |
| Diisopropanolamine (mg/ml) | 10 | 35 | — | — | — | — | — | — | — | — | — | — | — | — | — | — | — | — | — | — |
| 2-amino-2-methyl-1-propanol (mg/ml) | — | — | 4 | 10 | 22 | — | — | — | — | — | — | — | — | — | — | — | — | — | — | — |
| Monoethanolamine (mg/ml) | — | — | — | — | — | 10 | — | — | — | — | — | — | — | — | — | — | — | — | — | — |
| 1-dimethylamino-1-propanol (mg/ml) | — | — | — | — | — | — | 10 | — | — | — | — | — | — | — | — | — | — | — | — | — |
| 3-dimethylamino-1-propanol (mg/ml) | — | — | — | — | — | — | — | 10 | — | — | — | — | — | — | — | — | — | — | — | — |
| Diethylamine (mg/ml) | — | — | — | — | — | — | — | — | 10 | — | — | — | — | — | — | — | — | — | — | — |
| N,N—dimethylethanol amine (mg/ml) | — | — | — | — | — | — | — | — | — | 10 | — | — | — | — | — | — | — | — | — | — |
| Triethylamine (mg/ml) | — | — | — | — | — | — | — | — | — | — | 10 | — | — | — | — | — | — | — | — | — |
| Cetylpyridinium chloride (mg/ml) | — | — | — | — | — | — | — | — | — | — | — | 10 | — | — | — | — | — | — | — | — |
| Cocamidopropylamine oxide (mg/ml) | — | — | — | — | — | — | — | — | — | — | — | — | 21 | 43 | — | — | — | — | — | — |
| C20 Ammonium hexanoate (mg/ml) | — | — | — | — | — | — | — | — | — | — | — | — | — | — | 10 | — | — | — | — | — |
| Didecyldimethylammonium chloride (mg/ml) | — | — | — | — | — | — | — | — | — | — | — | — | — | — | — | 10 | 24 | 49 | — | — |
| Lecithin (mg/ml) | — | — | — | — | — | — | — | — | — | — | — | — | — | — | — | — | — | — | 10 | 10 |
| Rate Constant 80° C. | 0121 | 0350 | 0800 | 0607 | 0550 | 0505 | 0711 | 0800 | 0705 | 0600 | 0735 | 0701 | 0390 | 0350 | 0429 | 0633 | 0480 | 0500 | 0906 | 0884 |
| Predicted days to 90% at RT | 525 | 690 | 440 | 560 | 720 | 1050 | 525 | 440 | 530 | 555 | 500 | 530 | 650 | 700 | 390 | 590 | 800 | 690 | 375 | 425 |

*Estimates are less than 10 days

Substantially similar results are obtained when the erythromycin base in the above compositions is replaced, in whole or in part, by erythromycin estolate, erythromycin glucoheptonate, erythromycin lactobionate, erythromycin propionate, erythromycin stearate, erythromycin ethyl succinate, and mixtures thereof. Substantially similar results are also obtained where the zinc acetate or zinc octoate in the preceding formulations is replaced, in whole or in part, by toxicologically-acceptable zinc salts of other $C_1$-$C_{12}$ carboxylic acids, zinc salts of amino acids, zinc acetylacetonate, zinc chloride, zinc bromide, zinc citrate, zinc maleate, zinc benzoate, zinc phosphate, zinc sulfate, or mixtures thereof.

Using the experimental procedure outlined above and a zinc erythromycin component comprising mixtures of erythromycin base with zinc acetate or zinc octoate, the surfactants listed below were tested to determine their effect on the storage stability of the zinc erythromycin component. Those surfactants marked with a plus sign (+) provided a significant extension of storage stability when compared with similar compositions not containing the surfactants.

| Anionic Surfactants | Zwitterionic Surfactants |
|---|---|
| lauroyl sarcosine | +$C_{20}$ ammonium hexanoate |
| dioctylester of sodium sulfosuccinic acid (Aerosol OT commercially available from American Cyanamid Chemical Products Division) | cetyl ammonium sulfonic acid betaine |
| Nonionic Surfactants | Other Surfactants |
| Pluronic L35[1] | urea |
| Pluronic L31 | +diisopropanolamine |
| Pluronic L63 | 2-pyrilidinone |
| Pluronic L122 | povidone (1-ethenyl-2-pyrrolidinone polymer) |
| Pluronic L63 | Crodamol PMP (propoxylated (1) myristyl propionate commercially available from Croda, Inc.) |
| Pluronic L122 | |
| Pluronic F128 | |
| Pluronic F68 | +lecithin |
| Pluronic P103 | +N,N—dimethyltetradecylamine |
| Tween 40[2] | |
| Span 85[3] | +diethylamine |
| Cationic Surfactants | +2-amino-2-methyl-1-propanol |
| +didecyldimethylammonium chloride | +monoethanolamine nicotinamide |
| +cetylpyridinium chloride | +1-dimethylamino-2-propanol |
| +cocamidopropylamine oxide | +3-dimethylamino-1-propanol |
| | +N,N—dimethylethanol amine |
| | +triethylamine |

[1]Pluronics are block copolymers of ethylene oxide and propylene oxide commercially available from BASF Wyandotte Corp. The surfactants are coded as follows: P = paste form; L = liquid form; F = solid (flaked) form; first digit(s) indicate molecular weight of hydrophobic base molecule; last digit indicates approximate percentage of ethylene oxide in total molecule.
[2]polyoxyethylene (20) sorbitan monopalmitate commercially available from ICI Americas, Inc.
[3]sorbitan trioleate commercially available from ICI Americas, Inc.

EXAMPLE II

The mixing of a 60 liter batch of a composition of the present invention containing 4.6% (w/v) erythromycin base, 1.38% (w/v) zinc acetate, 2.0% (w/v) diisopropanolamine, 27.0% (v/v) diisopropyl sebacate and 67.0% (v/v) tertiary butyl alcohol is described below.

40.0 liters of tertiary butyl alcohol are poured into a stainless steel mixing vessel. 1.20 kilogram of diisopropanolamine is added to the same vessel and the mixture is mechanically agitated. 2.76 kilograms of erythromycin base (assuming an erythromycin potentency of 1,000 ug/mg) is added to the same vessel with continued agitation until the erythromycin is dissolved. 0.828 kilogram of zinc acetate is added to the vessel and stirring is continued until the zinc acetate is dissolved. The mixture is brought to volume by adding 16.2 liters of diisopropyl sebacate. Stirring is continued for a minimum of 5 minutes to insure adequate component mixing. The composition exhibits a pH of about 8.8.

This results in 1,935 bottles of product, assuming no in-process losses or samples. The product formed exhibits excellent effectiveness when used topically in the treatment of acne vulgaris and, further, exhibits excellent shelf-life storage stability.

In the above example, the tertiary butyl alcohol may be replaced, in whole or in part, with isoamyl alcohol, amyl alcohol, tertiary amyl alcohol, or mixtures thereof. Substantially similar results are obtained when the diisopropanolamine in the above example is replaced, in whole or in part, with didecyldimethylammonium chloride, cetyl pyridinium chloride, cocamidopropylamine oxide, $C_{20}$ ammonium hexanoate, lecithin, N,N-dimethyltetradecylamine, diethylamine, 2-amino-2-methyl-1-propanol, monoethanolamine, 1-dimethylamino-2propanol, 3-dimethylamino-1-propanol, N,N-dimethylethanolamine, triethylamine, triethanolamine, and mixtures thereof.

Similar results are also obtained where, in the above example, erythromycin base is replaced, in whole or in part, by erythromycin estolate, erythromycin glucoheptonate, erythromycin lactobionate, erythromycin propionate, erythromycin stearate, erythromycin ethyl succinate, and mixtures thereof. Similar results are also obtained when the zinc acetate component is replaced, in whole or in part, with other toxicologically-acceptable zinc salts of $C_1$-$C_{12}$ carboxylic acids, zinc salts of amino acids, zinc acetylacetonate, zinc chloride, zinc bromide, zinc citrate, zinc maleate, zinc benzoate, zinc phosphate, zinc sulfate, zinc octoate, or mixtures thereof.

What is claimed is:

1. A stable topical pharmaceutical composition comprising:
   (a) a safe and effective amount of zinc erythromycin comprising a mixture of a toxicologically-acceptable zinc salt and an erythromycin compound selected from the group consisting of erythromycin base, salts of erythromycin base with acids, and ester derivatives of erythromycin; and
   (b) from about 50% to about 99% of t-butanol.

2. A composition according to claim 1 which contains from about 0.3% to about 15% of component (a).

3. A composition according to claim 2 having a pH of from about 7 to about 10.

4. A composition according to claim 3 which contains from about 55% to about 80% of t-butanol.

5. A composition according to claim 3 which additionally contains from about 0.1% to about 10% of a pharmaceutically-acceptable stabilizer selected from the group consisting of diisopropanolamine, monoethanolamine, 2-amino-2-methyl-1-propanol, diethylamine, N,N-dimethylethanolamine, triethylamine, triethanolamine, cetyl pyridinium chloride, $C_{20}$ ammonium hexanoate, 1-dimethylamino-2-propanol, 3-dimethylamino-1-propanol, lecithin, and mixtures thereof.

6. A composition according to claim 5 which contains from about 0.5% to about 5% of the stabilizer component.

7. A composition according to claim 6 wherein the stabilizer component is diisopropanolamine.

8. A composition according to claim 6 which additionally contains from about 1% to about 45% of a pharmaceutically-acceptable cosolvent.

9. A composition according to claim 8 which contains from about 15% to about 35% of said cosolvent.

10. A composition according to claim 9 wherein the stabilizer component is diisopropanolamine.

11. A composition according to claim 10 wherein the cosolvent is diisopropyl sebacate.

12. A composition according to claim 11 wherein component is the reaction product of erythromycin base and zinc acetate.

* * * * *